United States Patent [19]

Eitenmuller et al.

[11] Patent Number: 5,108,399

[45] Date of Patent: Apr. 28, 1992

[54] DEVICE FOR OSTEOSYNTHESIS AND PROCESS FOR PRODUCING IT

[75] Inventors: Jurgen Eitenmuller, Brauweiler; Heinz Offergeld, Monchen-Gladbach; Walter Michaeli, Aachen, all of Fed. Rep. of Germany

[73] Assignee: Boehringer Ingelheim GmbH, Ingelheim am Rhein, Fed. Rep. of Germany

[21] Appl. No.: 407,986

[22] Filed: Sep. 15, 1989

[30] Foreign Application Priority Data

Sep. 17, 1988 [DE] Fed. Rep. of Germany ....... 3831657

[51] Int. Cl.⁵ .............................. A61F 5/04; A61F 2/28
[52] U.S. Cl. ........................................ 606/77; 623/16; 606/73; 606/76
[58] Field of Search ............... 128/69; 606/61, 65, 606/70, 73, 76, 77; 623/16, 16 A, 16 B, 16 C, 16 F

[56] References Cited

U.S. PATENT DOCUMENTS

| | | | |
|---|---|---|---|
| 4,177,524 | 12/1979 | Grell et al. | 606/73 |
| 4,476,590 | 10/1984 | Scales et al. | 606/76 |
| 4,648,388 | 3/1987 | Steffee | 128/69 |
| 4,687,675 | 8/1987 | Nakano et al. | 606/76 |
| 4,728,570 | 3/1988 | Ashman et al. | 606/76 |
| 4,781,183 | 11/1988 | Casey et al. | 623/16 |
| 4,898,186 | 2/1990 | Ikada et al. | 606/77 |
| 4,905,680 | 3/1990 | Tunc | 606/77 |
| 4,908,030 | 3/1990 | Linkow et al. | 623/66 |

*Primary Examiner*—Randall L. Green
*Assistant Examiner*—Paul Prebilic
*Attorney, Agent, or Firm*—Daniel Reitenbach; David E. Frankhouser; Mary-Ellen M. Timbers

[57] ABSTRACT

A resorbable osteosynthesis device consisting of: 1) a resorbable plate, in which the side of the plate facing the bone is coated with calcium phosphate and/or hydroxyl apatite; and 2) preferably, a resorbable fixing device consisting of a threaded bolt which is optionally coated with calcium phosphate and/or hydroxyl apatite, and a nut which can be fitted onto the threaded bolt.

13 Claims, 4 Drawing Sheets

DEVICE FOR OSTEOSYNTHESIS AND PROCESS FOR PRODUCING IT

The invention relates to a resorbable device for osteosynthesis consisting of an osteosynthesis plate and a fixing device and methods of producing them.

The use of stable plate osteosynthesis by means of which a mechanical connection is established between the two broken ends of a fracture is known per se and can be used to stabilise all kinds of fractures to the human skeleton. Conventionally, the plates, screws, nails or pins needed for the osteosynthesis are made from metal (stainless steels or chromium/nickel alloys (e.g. of type L 316)), which have essentially two serious disadvantages: on the one hand, the degree of stiffness of the metal implants is significantly greater than that of human bones. The resulting stress protection leads to bone breakdown (osteoporosis) which in turn increases the risk of another fracture once the metal plate has been removed. Moreover, after the healing process has ended, the implant has to be removed in another operation, which not only exposes the patient to additional risks but also takes a long time to heal. Moreover, the increasing number of chromium/nickel allergies occurring and the resultant complications present problems in using materials of this kind.

These disadvantages can be overcome by the use of so-called bio-resorbable polymers. Biologically resorbable polymers in general and in accordance with the invention are those polymers which under physiological conditions are broken down into substances naturally occurring in the body and are expelled with the metabolic circulation. The use of bio-resorbable materials in plate osteosynthesis has the advantage that there is no need for the second operation which would otherwise be necessary to remove the implant. The resorption-induced breakdown of the implant, which involves a corresponding reduction in mechanical stability and brings about an increasing functional loading of the bone which in turn permits further functional structuring in the point of fracture, thus prevents the undesirable effect of "stress protection".

Numerous patents and patent applications relate to resorbable implants for plate osteosynthesis: EP 0258 692, U.S. Pat. No. 4,655,777, EP 0204 931, EP 0011 528 and U.S. Pat. No. 4,329,743.

In these patents, it is taken as a premise that the strength of the resorbable polymers is insufficient for use in osteosynthesis. For this reason it has been proposed that fibres of various kinds be used as reinforcing material to increase the mechanical load capacity, whilst these fibres may consist of materials which are resorbable or, as a rule, non-resorbable. The shape of the plates or screws is taken almost entirely from the corresponding osteosynthesis devices made of metal. However, in practice it has been found that the shapes and constructions which have proved satisfactory for "metal osteosynthesis" have serious disadvantages when resorbable polymers are used. Thus, for example, no thought has been given to the fact that the possible designs resulting from the use of plastics permit other constructions which are substantially better adapted to stress and the use of which would make matters considerably easier for the operating surgeon. Conventional osteosynthesis plates consisting of resorbable polymers have for example the disadvantage that they break relatively easily, particularly in the region of the screw holes.

The embodiments hitherto proposed for screws in the prior art also have disadvantages, such as the fact that a very great range of screw lengths must be available to satisfy the requirements of each individual fracture. The length of the screws required is currently determined using measuring sensors at holes pre-drilled in the bones in question. This presupposes a great deal of experience on the part of the operating surgeon. Depending on the length measured, suitable screws can then only be selected during the operation. When metal screws are used, a further disadvantage is the fact that when the screws are tightened, the thread may be stripped in the bone, which means that either a replacement hole has to be drilled or a new screw of larger diameter has to be used, which cannot be inserted until the original screw has been removed, with considerable difficulty. On the other hand, when screws made from resorbable materials are used there is the disadvantage that although the thread in the bone is not destroyed when the screw is tightened, because of the low mechanical strength the thread of the screw itself will be stripped or the screw will be broken off below the screw head. These screws then have to be drilled out and subsequently replaced.

This comparatively low mechanical stability means that the screws made from resorbable polymers cannot be tightened, when securing the plate, sufficiently to achieve the required minimum movement between the plate and the bone halves, and consequently the satisfactory growing together of the fragments of bone cannot be guaranteed. The less free mobility there is between the pieces of bone (relative displacement), the better the prospects of healing of the fracture.

A further disadvantage of resorbable synthesis screws is the fact that they do not produce any X-ray contrast and consequently the operator has no way of assessing the correct position of the screws.

The aim of the present invention is to provide a resorbable device for osteosynthesis which reduces the relative displacement between the plate and the fragments of bone to the degree necessary for the bones to grow together again without any complications.

A further aim of this invention is to provide devices for securing the osteosynthesis plate of resorbable polymer which, in the event of its becoming damaged or destroyed, can easily be removed from the bone and replaced, so as to avoid the possible need to remove the entire fixing device.

A further aim of this invention is to provide fixing devices which, in terms of their length, can be fitted into the drilled hole without any further ado, so as to do away with the need to have a supply of a variety of screws or fixing devices.

A further object of the present invention is to provide a design for the fixing device which is specially adapted to the use of plastics, and which permits higher tightening forces compared with plastic fixing devices which are mere copies of the metal kind.

A further object of the present invention is to make an osteosynthesis device of resorbable polymer which shows up under X-ray.

The aim of the present invention is achieved by means of a resorbable osteosynthesis device consisting of a plate of resorbable polymer or copolymer provided with screw holes, which is coated on the side facing the bone with calcium phosphate and/or hydroxyl apatite granules and at least two fixing devices consisting of a threaded bolts and an associated nut.

Examples of suitable resorbable polymers from which the plate, threaded bolts and nuts may consist include polymers and copolymers based on the following monomers: L-lactide, D, L-lactide and glycolide. If desirable or necessary, the polymers or copolymers may be reinforced with resorbable fibres. The processes for producing and processing suitable polymers and copolymers are known from the prior art and need not be explained more fully here.

The shape of the plate according to the invention may be varied as desired within very wide limits, provided that this does not conflict with the properties of the polymer materials used (breaking strength, rate of decomposition, etc.) and the particular use intended (nature of fracture etc.). An essential feature of the plate according to the invention is that on its underside, i.e. the side closest to the bone, it has a coating of calcium phosphate and/or hydroxyl apatite, preferably in the form of granules or small pellets.

On the one hand, the underside of the plate according to the invention is provided by this coating with a roughened surface which ensures reduced relative displacement compared with the osteosynthesis plates of bio-resorbable materials used hitherto, with the same contact pressure, and on the other hand the plate coated with calcium phosphate or hydroxyl apatite ensures rapid incorporation on the bone surface, since industrially produced calcium phosphate ceramics granules are highly similar to the mineral found in bone.

The accretion of the bio-resorbable osteosynthesis plate, coated with calcium phosphate ceramic granules, on the bone surface results in additional mechanical stabilisation of the plate on the bone surface, which at the same time minimizes the undesirable movement between the bone and plate at a given axial screw tension. This may be of critical importance if premature breakage of the fixing device occurs (this device being referred to hereinafter as a threaded bolt or screw) as a result of resorption starting and consequently mechanically weakening the screws, whilst it can be assumed that resorption will happen more quickly with filigree screws subjected to high mechanical load than with the substantially more solid plates.

As a result of the coating of calcium phosphate or hydroxyl apatite (hereinafter also referred to as calcium phosphate ceramics granules) there is also the possibility of making the implant visible under X-ray. In this way, the size and shape of the implant including its position relative to the stabilised bone can be evaluated on an X-ray image. Any breakage or subsequent dislocation of the plate can also be detected by X-ray. The calcium phosphate ceramics are also resorbable, although this will take rather longer than is the case with polylactide, for example.

The plate according to the invention may be produced using the following techniques:

The calcium phosphate ceramics granules are pressed hot into the surface of a prefabricated plate. The use of this method results in a mechanically very strong bonding of the granules to the carrier. However, the granules may also be applied for example, by pressing a polylactide film with a thickness of 0.5 to 1.0 mm onto a hot, firmly based layer of granules, so as to bond the film to the granules. It has proved advantageous if the granules are not lying too close together; this is to ensure that the granules do not fly off when the plates are bent. The granule-coated polylactide film thus obtained is placed in a suitable injection moulding tool and polylactide is injected therein, so that the polylactide film coated with hydroxyl apatite or with calcium phosphate is intimately connected to the implant member produced by injection moulding. The granule-coated film may be produced in large sheets. The film can be cut to the required plate size in a subsequent operation.

In another embodiment, the calcium phosphate ceramic granules may be electrostatically fixed to a wall of the tool and then the material injected over them as described above. There is also the possibility of producing the coating by holding the granules in position on small bores of an injection mould which are smaller in diameter than the granules, by applying suction to them throughout the subsequent injection moulding operation. The plates according to the invention may be deformed by heating, so that they can be fitted to the bone surface. This may also be carried out by the operating surgeon in the operating theatre, e.g. using a special hot air blower or a microwave generator specially adapted for this purpose. The granule coating does not break off to any appreciable extent. The spontaneous maximum tensile force of 2000N measured with a Zwick material testing machine on a polylactide plate used in the tests was unaltered after the heat treatment of the surface.

In another embodiment, all the surfaces of the plate which are not facing the bone, including those of the screw heads, may be coated with a low molecular film of a suitable polymer, e.g. a polylactide film, having only low mechanical strength, this film containing colloidally distributed silver. The surface coating—of a thickness of up to 1 mm—on the one hand prevents the surface of the implant from being colonised by bacteria in the first weeks after the operation, owing to the oligodynamic antibacterial activity of silver; and on the other hand the implant is rendered visible as a shadowy shape under X-ray. To avoid primary tissue toxicity, it is necessary for those layers closer to the plate to have a higher silver content than the surface layers. The more highly concentrated but deeper layers will not have any toxicologically harmful effect since in the course of resorption amounts of silver will be released from the deeper layers, so that after the layers on the surface have been eroded away, the tissue will come into contact with a layer which contains an already reduced concentration of colloidal silver, in relation to the initial concentration, thus avoiding damage to the tissue.

In a further embodiment, the calcium phosphate ceramic granule coating of the plate may itself be enriched with fine-grained silver phosphate in an amount of up to 30% (based on the total weight of the granules), to achieve an antibacterial activity on this side of the implant as well.

Instead of colloidally distributed silver the layers described may also contain PVP-iodine [polyvinyl-pyrrolidone-iodine complex or poly(1-vinyl-2-pyrrolidin-2-one)-iodine complex] in concentrations of from 5% to 40%, whereby an antibacterial activity is achieved as well a making the plate visible under X-ray.

Antibacterial or bacteriostatic activity may also be achieved by treating with thermostable antibiotics selected from various groups, reference being given to those antibiotics with a broad spectrum of activity such as aminoglycosides, gyrase inhibitors or vancomycin. In a coating of this kind, no attention need be paid to systemic toxicity, since only small amounts are detectable in the serum, far below the toxicity limits which have to be observed for intravenous administration.

The plate itself is subjected essentially to bending and tensile stress, as is known from the development of metal plates for stabilising bones. It is therefore desirable to achieve longitudinal orientation of the chains of molecules in the injection moulding process by a suitable arrangement of the injection nozzles. The technical prerequisites for processing polymers are known to those skilled in the art. However, it should be pointed out that the material to be injection moulded must be kept extremely dry since, at higher temperatures the proportion of chain breakdown products increases with every percentage increase in the water content. This has a direct effect on the degradation characteristics of the polymer. As already mentioned, there is the possibility of adding powdered thermostable antibiotics such as aminoglycosides or gyrase inhibitors. Since the thermal loading thereof becomes acute only for an extremely short time during the pressing operation, the permissible upper temperature limit specified by the manufacturer can be exceeded without causing severe disadvantages to the preparation or to the implant.

The control of the temperature and subsequent injection during the hardening process should be carried out so that no cavities are formed in the centre and the heat can be conducted away as rapidly as possible so as to minimise the thermal stress on the polymer.

In a particular embodiment, the plate according to the invention is reinforced by a fibre material incorporated in the polymer.

The preferred fibre material is stretch poly-L-lactide, whilst the matrix preferably consists of poly-D,L-lactide. The tensile strength of the plates of this embodiment of the invention is greater than that of the non-reinforced plate by up to a factor of 10. It has proved advantageous to use extruded fibres which are additionally stretched during hardening. Since the plates are subjected essentially to tensile and bending stresses, the fibres should be longitudinally oriented and the angle between the fibres should not exceed 30°. As a temperature protection for the fibres during manufacture, a thin coating of low molecular L-lactide or D,L-lactide may possibly prove advantageous. Colloidally distributed silver, PVP-iodine or a heat-resistant antibiotic in powder form may be added to the reinforced plate.

The shape of the plates will depend primarily on the field of application. In spite of the different lengths or generally different sizes of the plates—depending on the planned use—osteosynthesis plates and the fixing devices preferably take the following basic forms:

Depending on the intended use or type of application, different dimensions of plates or heights of convexity may be more advantageous.

Figure 1A:
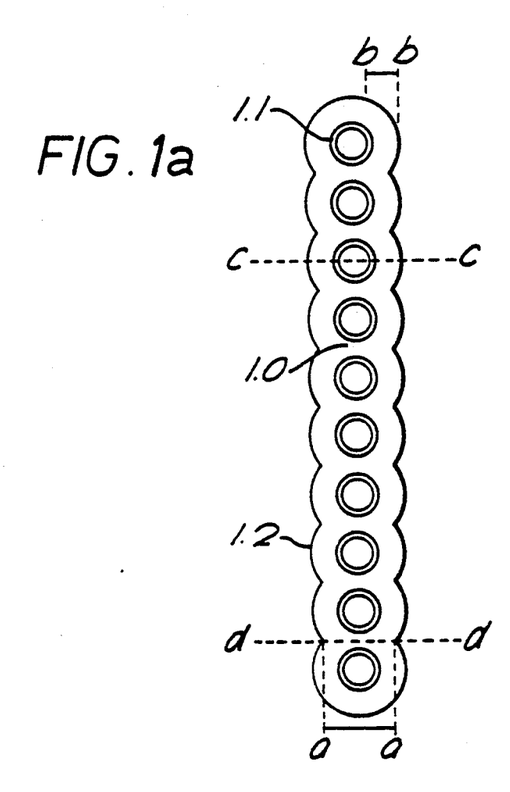
FIG. 1a shows a preferred embodiment of the osteosynthesis plate according to the invention (1.0).
Figure 1B:
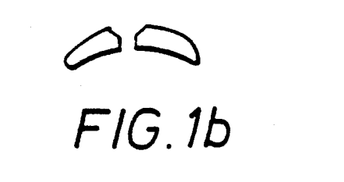
FIG. 1b shows a cross-section through the osteosynthesis plate according to the invention (1.0) from FIG. 1a along section line cc.
Figure 1C:
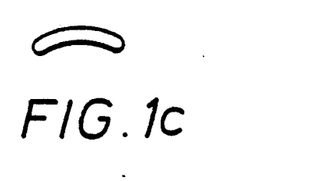
FIG. 1c shows a cross-section through the osteosynthesis plate according to the invention (1.0) from FIG. 1a along section line dd.
Figure 2:
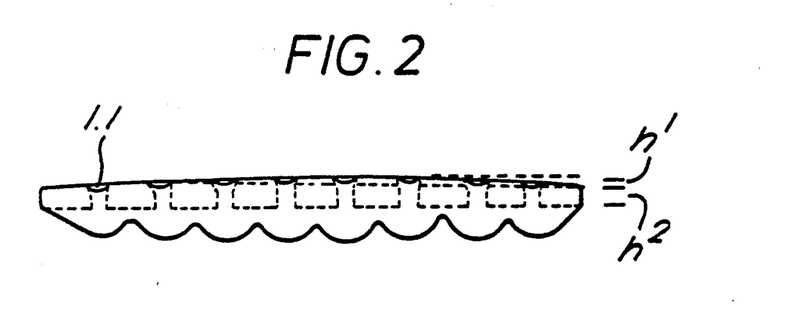
FIG. 2 shows a side elevation of the osteosynthesis plate according to the invention which is approximately 25% thicker in the centre than at the ends ($h^1 = \frac{1}{4}h^2$).

The plate (1.0) in FIG. 1 is of a configuration such that the cross-section along the section line bb, in other words the cross-sections along the section line cc which can pass through the central point of the screw holes or fixing holes (1.1), correspond to approximately half the cross-section along the section line dd in the position aa of the plate (1.0) between the fixing holes (1.1). This shape avoids premature "weakening" of the plate (1.0) in the region of the fixing holes (1.1) as a result of decomposition of the polymer material by resorption. As a result, the osteosynthesis plate has an elongate basic shape which has outwardly convex portions (1.2) in the region of the fixing holes Furthermore, the plate should be 25% thicker in the centre than at its ends (FIG. 2). Moreover, stabilisation of the plate is achieved by means of lateral and longitudinally extending reinforcements or thickened portions of the plate (7.1 in FIGS. 7a–d) essentially in the central part of the plate.

These reinforcements or thickened portions should only be a height such that they do not project above the highest point of the screw, to ensure that they do not lead to an overall thickening of the plate/screw system. The depressions for the fixing holes are preferably of spherical configuration (FIG. 1b), whilst oblong holes with an inclined approach surface may possibly prove advantageous.

The osteosynthesis plate according to the invention is joined to the bone by means of a fixing device.

Suitable fixing devices include screws in general, threaded pins, nuts or similarly shaped fixing devices having the same function, consisting of a polymer which is resorbable in the body, such as poly-L-lactide, poly-D,L-lactide, polyglycolide, copolymers or polymers or copolymers with resorbable fibres.

When manufacturing the screws it has proved advantageous to provide them with a 3 degree-30 degree sawtooth thread suitable for plastics. This thread has the advantage that the turns of thread in the centre of the screw have the same thickness relative to the turns of thread in the bone and in the screw nut. The edges of the thread are rounded so as to avoid premature loss of the holding force, such as may be observed in sharp edged threads, which is the case with most threads, as a result of resorption. The 3 degree-30 degree sawtooth thread has a low restoring torque, which prevents the screws from loosening in the course of the microscopic movements which take place continuously in the human or animal body, since the turns of thread which are to be subject to very broad stresses are broadly supported on the surrounding bone.

In general, the material properties of the screws can be improved by the use of injection moulding methods such as are used to produce composite fibre materials. A helical 45° rotation in the dextrorotatory direction must be achieved both in the orientation of the chains of molecules in the centre of the screw and also in the orientation of the fibres when producing the compound material, to ensure that the screw is able to withstand both the axially longitudinally directed helical tension as well as the rotational force which has to be withstood at the same time. A fundamental improvement in the material is achieved by the use of the injection moulding method (denser packing of the material as well as crosslinking of the chains of molecules).

If conventional screws are used, which are turned in order to achieve an axial screw tension with the application of a suitable torque, the following shapes of screw heads may be suitable, for example:

An internal hexagonal shape extending as far as the point of attachment of the centre of the screw and consequently extending through the entire screw head and surrounded by an external hexagon (of flatter construction). Further depressions are formed in the circularly extending wall of the screw head, which make further transmission of the torque possible.

With a screw head of this kind and a corresponding screwdriver, the screw can be reliably guided (the screw is located on the screwdriver and can also be inserted in downwardly directed bores). This embodiment also ensures maximum torque transmission without running the risk of stripping off the edges in an attempt to transfer the torque from the screwdriver to the screw. Screw heads of this kind can readily be produced in large numbers at low costs by the injection moulding method.

Figure 3:
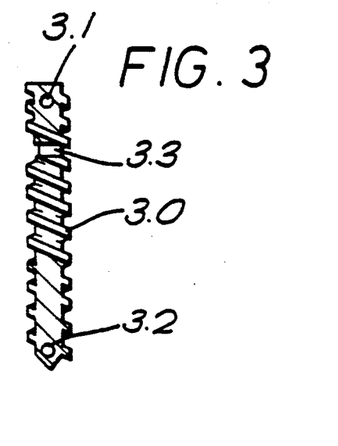
FIG. 3 shows the threaded bolt (3.0) of the fixing device according to the invention, which has a transverse hole (3.1), a particle (3.2) which generates an X-ray contrast and a tapered portion (3.3) (frangible point).
Figure 4:
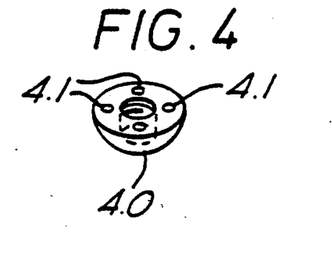
FIG. 4 shows a preferred embodiment of a nut (4.0) of the fixing device according to the invention, which optionally has a plurality of devices (4.1) for transmitting a torque.

The resorbable fixing device according to the invention consists of a threaded bolt (3.0) (FIG. 3) and an associated nut (4.0) with an internal thread (FIG. 4), whilst at one end of the threaded bolt there is the facility of a tool attachment for the transmission of torque (e.g. (3.1) in FIG. 3).

This attachment may be the thread itself, but is preferably in the form of a hole, slot or internal or external hexagon. The fixing unit may be screwed into the bone and tightened using any suitable tool, the tightening force of which should be regulatable. In a preferred embodiment, the threaded bolt (3.0) should have a frangible point (3.3) (FIG. 3) which enables the fixing unit to be replaced without any trouble if the threaded bolt should fail when being inserted.

The lower end of the threaded bolt (3.0) (FIG. 3) may be provided with a material or particles (3.0) (FIG. 3) which generates an X-ray shadow, as will be described hereinafter, this material being provided in a finely divided layer on the surface or in compact form inside or simply on or in the tip of the screw or threaded bolt (FIG. 3). The material which generates the X-ray shadow may itself be bioresorbable or non-bioresorbable.

There are various methods of fixing the plate according to the invention, depending on the construction of the threaded bolt or pin.

a) The threaded pin contains no special arrangements for the attachment of a tool (i.e. means for turning the threaded pin). In this case, a specially designed implement is needed to screw it in.

Screwed on to the top end of the threaded pin is a nut having a hexagonal shape and converying spherically at the lower end. The nut is inserted, together with the threaded pin located thereon, into the hexagonal recess of a special device and the thread is screwed through the nut into the internal thread inside the device.

In this position, the threaded pin can be inserted into the bone by rotation of the knurled nut on the device, after which the threaded pin is tightened until finger tight. Then the threaded pin is tightened by means of a bracing mechanism, whilst at the same time the instrument is supported on the plate up to a value 10% below the tear strength.

This position is secured as follows:

By means of a second knurled screw of the device the nut is screwed downwards until finger tight so that the nut rests on the plate and takes over the axial screw tension hitherto maintained by the device. In this way, there is no torque load on the threaded pin since the axial screw tension is applied by pure tension on the screw end screwed into the device, whilst the nut only has to be screwed downwards until it picks up and maintains this axially formed screw tension.

The apparatus is then released and the projecting threaded pin is cut away above the nut by means of a hot wire. The hot wire may at the same time be passed transversely through the threaded pin and the nut in order to achieve welding which will prevent the screw fixing from becoming loose.

The screwed-in threaded pin may also be fixed in a suitable manner for the plastics material, for example by means of a projecting peg which may be machined so as to be round or angular and has fine teeth directed downwardly (i.e. towards the plate or the bone) on the inside. A suitably sized sleeve with similar teeth but arranged in the opposite direction is fitted over this, and pushed towards the plate by the application of downwardly directed tension, and by the engagement of the teeth with one another a mechanically strong connection suitable for plastics is produced which maintains the axial screw tension. This sleeve should be constructed like a telescoping elastic spring, so as to engage spontaneously with the teeth when the sleeve is pushed downwards.

b) The threaded pin contains a specially shaped attachment for the application of a tool or a device for turning the threaded pin.

In another embodiment, the device for fixing the osteosynthesis plate may consist of a threaded pin (3.0) (FIG. 3) and a nut (4.0) (FIG. 4), whilst the threaded pin made from a resorbable polymer is provided at its upper end with an attachment, such as a hexagon, rectangle, socket or transverse hole (3.1) (FIG. 3) to enable the threaded pin to be rotated into the bone. In a preferred embodiment, the threaded pin is provided, on the opposite end of the head of the thread (at the tip) designed for the transmission of torque (FIG. 3), with one or more particles (3.2) which produce one or more X-ray shadows, the or each particle consisting of a resorbable material or a non-resorbable material. The or each particle producing the X-ray shadow may however be arranged in the screw or in the threaded pin in a different way, as described hereinafter. The threaded pin itself is provided with a frangible point (3.3) which will enable the remainder of the threaded pin still located in the thread to be removed easily in the event of damage or premature breaking off.

Figure 5:
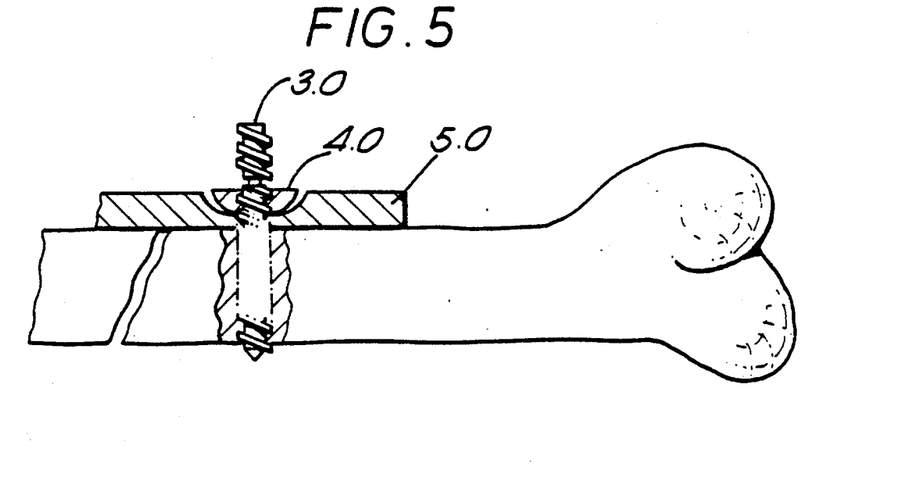
FIG. 5 shows an osteosynthesis plate according to the invention (5.0) which is mounted with the fixing devices according to the invention, the threaded bolt (3.0) and the nut (4.0) on the fragments of bone.
Figure 6:
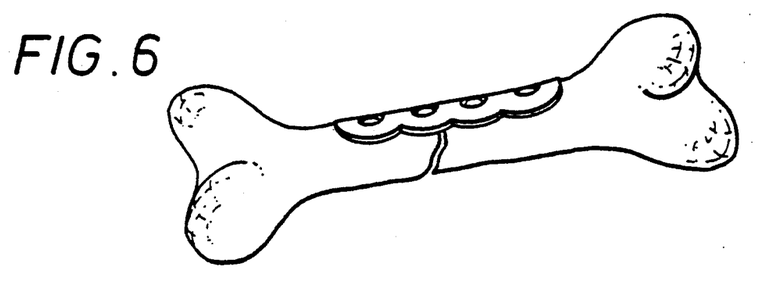
FIG. 6 shows the device according to the invention for osteosynthesis after the threaded bolts has been cut off.
Figures 7A, 7B, 7C:
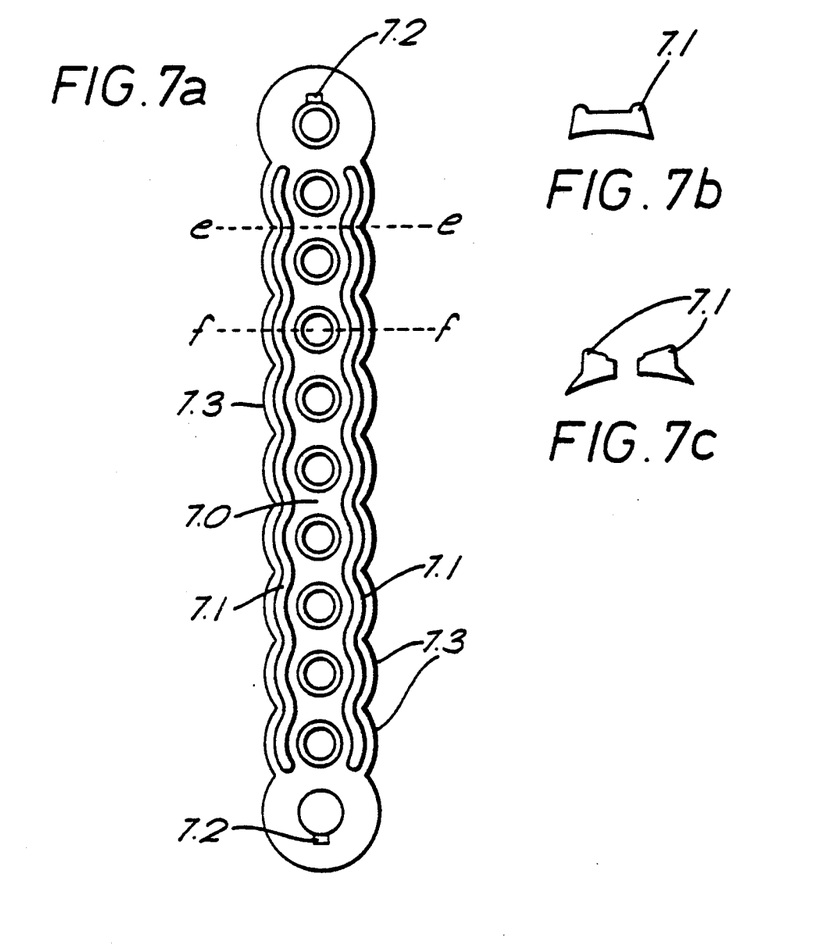
FIG. 7a shows another preferred embodiment of an osteosynthesis plate according to the invention (7.0), which is provided in its central portion with reinforcements (7.1) running parallel to the longitudinal direction and has widened portions in the region of the screw holes (7.3). The osteosynthesis plate (7.0) according to the invention has indentations (7.2) at both ends for the application of a plate clamping device.
FIG. 7b shows a cross-section through the osteosynthesis plate (7.0) according to the invention shown in FIG. 7a along the section line ee.
FIG. 7c shows a cross-section or the resulting cross-sectional areas of a section through the osteosynthesis plate according to the invention (7.0) from FIG. 7a along section line ff.
Figure 7D:
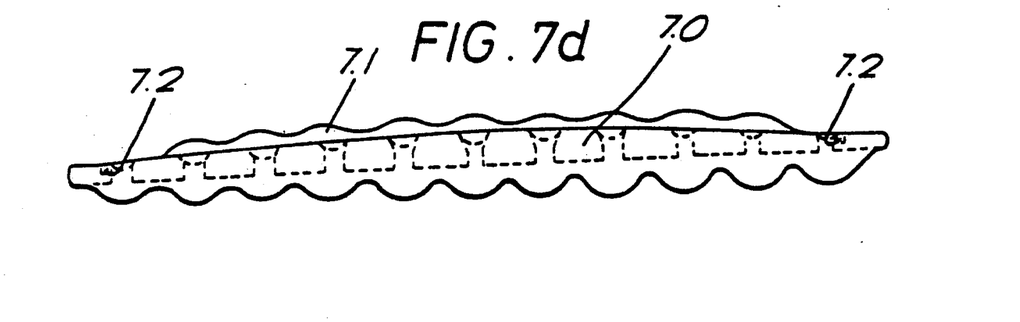
FIG. 7d shows a side elevation of the osteosynthesis plate (7.0) according to the invention from FIG. 7a with the reinforcement (7.1) and the indentations (7.2) for the application of a plate clamping device.
Figures 8A, 8B, 8C, 8D:
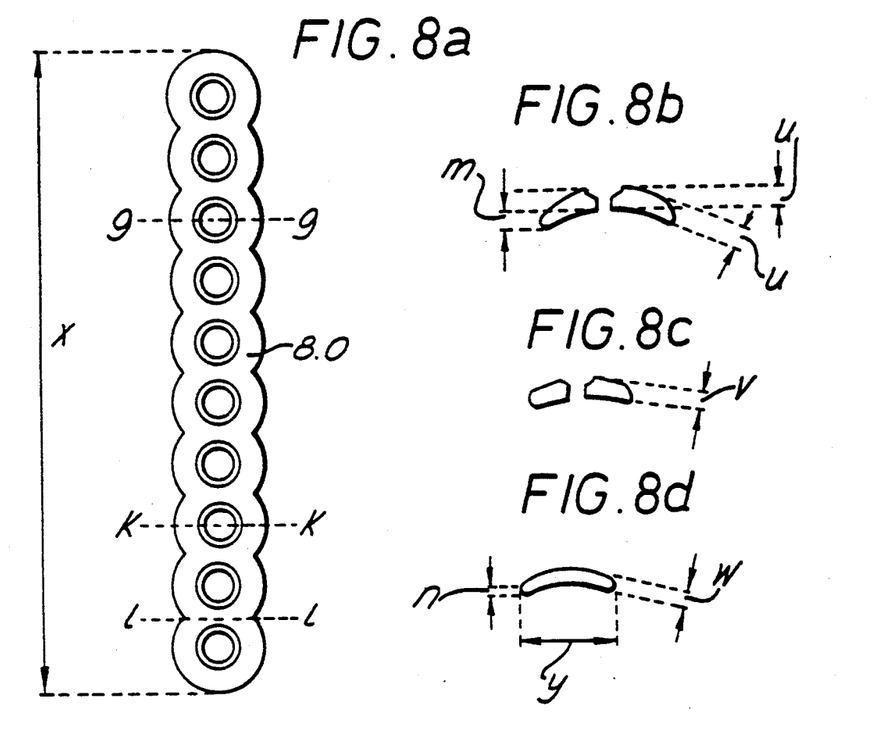
FIG. 8a shows another preferred embodiment of the device for osteosynthesis according to the invention in the form of an outer ankle plate (8.0) with the section lines gg, kk and ll, the length x of the plate amounting to about 10 cm.
FIG. 8b shows a cross-section through the osteosynthesis plate (8.0) according to the invention from FIG. 8a on the section line gg, the thickness u of the plate being about 2 mm and the height of the convexity m being about 2 mm.
FIG. 8c shows a cross-section through the osteosynthesis plate (8.0) according to the invention from FIG. 8a along section line kk, the thickness of the plate v being about 1.8 mm.
FIG. 8d shows a cross-section through the osteosynthesis plate (8.0) according to the invention from FIG. 8a along the section line 11, the thickness w of the plate being about 1.5 mm and the height n of the convexity being about 1 mm.
Figure 8E:
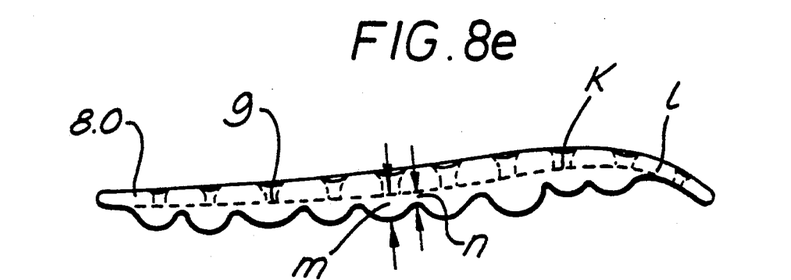
FIG. 8e shows a side elevation of the outer ankle plate (8.0) with the positions of the cutting planes in FIG. 8a and the height of the convexities m and n.

The threaded pin is screwed into the bone by means of a pin inserted through the transverse hole. The threaded pin is tensioned by means of an auxiliary tool which engages the thread of the threaded pin and is supported on the plate (5.0) (FIG. 5), and this threaded pin is then secured via the counter-member (4.0).

There are considerable advantages in the division of the screws hitherto used in the prior art, into a type of threaded pin and a type of nut:

By using threaded pins the maximum biasing force which could be achieved with screws can be almost doubled.

The threaded pin can be screwed into the hole prepared in the bone until the particle or particles inserted in the pin and producing an X-ray contrast show on the X-ray screen that the threaded pin has been inserted deeply enough. After the counter-member (4.0) with an internal thread has been screwed up, the threaded pin is tensioned to the desired tensioning force by means of an auxiliary device which engages, for example, with the apparatus (3.1) (FIG. 3) provided for transmitting torque, and the counter-member (4.0) (FIGS. 4 and 5) is tightened, although this does not require the application of great torque since only the frictional forces occurring in the thread have to be overcome, but there is no need to apply bias through the tightening moment, and consequently the torsional moment which would otherwise be present in the screw during tightening is reduced substantially, and finally there are really only tensional forces in the threaded pin. The attainable tightening forces in the fixing unit can thus assume greater values.

After the plate has been fixed, the projecting ends of the various pins can be cut off, whilst any chips or fragments which may under certain circumstances enter the wound need not be removed, as is the case with metal chips, for example, since they will not cause any irritation of the tissue and will be absorbed by the body in the course of time. However, as described above, the projecting pins may also be removed by means of a hot wire, thus ensuring that no chips are formed and at the same time a heat seal is achieved which prevents the screw fixing from becoming loose.

If fibre-reinforced materials are used, because of the virtually unidirectional action of forces, the fibres can be introduced axially into the threaded pins, thus substantially improving the strength compared with screws subjected to torsion and tension, as well as simplifying the manufacturing process.

Screws of this kind, for example produced by injection moulding, also have better strength because of the orientation applied in the axial direction.

Since, in osteosynthesis materials consisting of resorbable polymers, unlike the corresponding osteosynthesis devices made of metal, it is not the bone which is the weakest member but the fixing unit, if the fixing unit is over-tightened it is the screw and not the bone which is damaged. Since the end of the pin projects clearly out of the plate in the solution according to the invention, a frangible point can be produced by means of a tapered portion (3.3) (FIG. 3) provided on the threaded pin, so that in the event of overloading the pin will break at this predetermined point. This broken threaded pin can readily be unscrewed by hand, without any further manipulations of the plate and without even removing it, whereas in other circumstances, if it were subsequently necessary to use a screw with a larger thread diameter, all the screws already inserted would automatically have to be removed.

A preferred embodiment of the fixing unit according to the invention is illustrated in FIGS. 3, 4, 5 and 6 and explained more fully hereinafter:

The threaded bolt (3.0) (FIG. 3) has, at its end provided for the transmission of torque, a transverse hole (3.1) for receiving a pin, the pin being capable of being inserted or screwed into said hole. At the opposite end, namely the tip, a particle (3.2) is provided which produces an X-ray shadow. The tapered portion (3.3) formed is in the form of a groove in this example, but may also take any other suitable form.

The counter member (4.0) (FIG. 4) is hemispherical in shape on one side in order to allow the use of screws which are not perpendicular to the plate. On the opposite side the counter-member (4.0) (FIG. 4) has four boreholes (4.1), which are intended to allow the insertion of screws with a suitable auxiliary tool.

The threaded bolt is screwed into the bone, by means of a pin inserted through the transverse hole (3.1), until the correct position of the screw (FIG. 5) is determined by X-ray. The threaded bolt is tensioned by means of an auxiliary tool which engages in the thread of the pin and is supported on the plate (5.0), and the threaded bolt is then secured by means of the counter-member (4.0).

The projecting ends of the threaded bolt are then cut off.

The holes may be drilled in the fragments of bone using a drilling template or jig which is placed over the holes in the osteosynthesis plate.

The invention further relates to the manufacture of screws or threaded bolts which may be made visible under X-ray, as already mentioned.

The screws or threaded bolts are given a small bead of calcium phosphate pressed into the tip, with heating, so as to be visible under X-ray. This enables the length of the screws to be determined in an X-ray and thus provides the operating surgeon with a method of monitoring so as to enable him to judge whether a screw is too long because of inaccurate measurement of its length during the operation.

No loss of strength need be feared since only the tip of the screws is gently heated.

Another possibility is to provide a plurality of pellets of calcium phosphate granules starting from the tip at intervals of 2 to 3 mm. A screw of this kind makes it possible to determine the position of the screw or its length even after it has been shortened, in an X-ray taken immediately post-operatively. In another embodiment, a rod of calcium phosphate (with a diameter of up to about 1 mm) about 5 mm long is introduced into the centre of the screw, again making it possible to determine the length and position of the screw in an X-ray, even after the screw has had to be shortened.

In another embodiment, very fine granules of calcium phosphate (granule diameter up to a maximum 300 μm) are applied on the distal half of the surface of the screw in the outermost layer thereof in the region of the turns of screw thread, so that these can also be made visible under X-ray.

The granules are intended to be applied only in the distal region of the screw, in order to avoid weakening of the screw too much. Apart from the advantage that even after the screw has been shortened, which may be necessary in the course of the operation, its geometric shape and position can be determined by X-ray, this embodiment has the advantage that the coating of the screw surface in the distal threaded region enables the screw to grow onto the corresponding bone surface, thus virtually ruling out any loosening of the screw caused by microscopic movements of the body or even the screw becoming unscrewed on its own.

What is claimed is:

1. A resorbable osteosynthesis device comprising:
   a) a resorbable plate;
   b) a coating on the plate comprising calcium phosphate, hydroxyl apatite, or a combination of calcium phosphate and hydroxyl apatite, wherein the coating is present on the portion of the plate which will be in contact with a fractured bone when the plate is in use; and
   c) resorbable means for fastening the plate to a fractured bone.

2. A resorbable osteosynthesis device as recited in claim 1 wherein the resorbable means for fastening the plate to a fractured bone is a fixing device comprising:
   a) a resorbable threaded bolt; and
   b) a resorbable nut capable of screwing onto the threaded bolt.

3. A resorbable osteosynthesis device as recited in claim 2 wherein the threaded bolt is coated with calcium phosphate, hydroxyl apatite, or a combination of calcium phosphate and hydroxyl apatite.

4. A resorbable osteosynthesis device as recited in claim 1 wherein the plate is constructed from a polymer or copolymer based on poly-L-lactide, poly-D,L-lactide or polyglycolide.

5. A resorbable osteosynthesis device as recited in claim 1 wherein the plate comprises reinforcing fibers.

6. A resorbable osteosynthesis device as recited in claim 1 wherein the plate is additionally coated with a film comprising colloidally distributed silver.

7. A resorbable osteosynthesis device as recited in claim 1 wherein the plate is additionally coated with a pharmaceutically active material.

8. A resorbable osteosynthesis device as recited in claim 7 wherein the pharmaceutically active material is a bactericidal or bacteriostatic agent.

9. A resorbable osteosynthesis device as recited in claim 1 wherein the plate comprises: i) a central portion with reinforcements running parallel to the longitudinal direction of the plate, and ii) widened portions about the means for fastening.

10. A resorbable osteosynthesis device as recited in claim 1 wherein the portion of the plate which will be in contact with a fractured bone when the plate is in use, has a transverse convexity.

11. A resorbable osteosynthesis device as recited in claim 2 wherein the threaded bolt comprises a means for turning the threaded bolt.

12. A resorbable osteosynthesis device as recited in claim 2 wherein the threaded bolt produces an X-ray contrast.

13. A resorbable osteosynthesis device as recited in claim 2 wherein the threaded bolt has a frangible point.

* * * * *